United States Patent
Hunt et al.

(10) Patent No.: US 6,930,125 B2
(45) Date of Patent: Aug. 16, 2005

(54) AIRWAY ALKALINIZATION AS A THERAPY FOR AIRWAY DISEASES

(76) Inventors: John F. Hunt, 1167 Raintree Dr., Charlottesville, VA (US) 22901; Benjamin M. Gaston, 794 Woodland Rd., Charlottesville, VA (US) 22901

( * ) Notice: Subject to any disclaimer, the term of this patent is extended or adjusted under 35 U.S.C. 154(b) by 0 days.

(21) Appl. No.: 10/181,840

(22) PCT Filed: Jan. 12, 2001

(86) PCT No.: PCT/US01/01062

§ 371 (c)(1),
(2), (4) Date: Jul. 8, 2002

(87) PCT Pub. No.: WO01/51046

PCT Pub. Date: Jul. 19, 2001

(65) Prior Publication Data

US 2003/0013695 A1 Jan. 16, 2003

Related U.S. Application Data

(60) Provisional application No. 60/176,388, filed on Jan. 14, 2000.

(51) Int. Cl.⁷ .............................................. A61K 31/40
(52) U.S. Cl. ........................ 514/423; 514/499; 514/712; 514/172; 514/178; 514/179
(58) Field of Search ................................. 514/423, 499, 514/712, 172, 178, 179, 649, 174, 598, 707, 427, 599, 460; 424/489, 54, 49, 85.5

(56) References Cited

U.S. PATENT DOCUMENTS

| | | |
|---|---|---|
| 5,116,861 A | 5/1992 | Goto et al. |
| 5,547,994 A | 8/1996 | Barberich et al. |
| 5,877,203 A | 3/1999 | Medford et al. |
| 5,906,811 A | 5/1999 | Hersh |
| 6,083,515 A | 7/2000 | Garvey et al. |
| 6,184,217 B1 | 2/2001 | Engber et al. |
| 6,187,344 B1 | 2/2001 | Eljamal et al. |
| 6,197,762 B1 | 3/2001 | Garvey et al. |
| 6,207,703 B1 | 3/2001 | Ponikau |

*Primary Examiner*—Zohreh Fay
(74) *Attorney, Agent, or Firm*—Woods, Rogers, PLC; Peter E. Rosden (57) ABSTRACT

The present invention relates to a method of treating asthma by raising the pH of the airways of an individual. The effect can be mediated directly by administering a pharmaceutically acceptable basic solution or alternatively, the effect can be mediated by enhancing the activity of glutaminase.

10 Claims, 4 Drawing Sheets

Days after Rhinovirus Innoculation

FIG. 5 B

Days after Rhinovirus Innoculation

AIRWAY ALKALINIZATION AS A THERAPY FOR AIRWAY DISEASES

This application claims the benefit of provisional application No. 60/176,388, filed on Jan. 14, 2000.

US GOVERNMENT RIGHTS

This invention was made with United States Government support under Grant No. RO18L59337-01, awarded by The National Institutes of Health. The United States Government has certain rights in the invention.

FIELD OF THE INVENTION

The present invention is directed to methods and compositions for treating asthma and other airway diseases. In particular, the present invention is directed to compositions and methods that raise the pH of the bronchial airways to alleviate the symptoms associated with asthma and other airway diseases.

BACKGROUND OF THE INVENTION

Concentrations of reactive oxygen and nitrogen species are high in the expired air, condensed breath and bronchoalveolar lavage fluid of patients with asthma. The bioactivities of many of these compounds in the asthmatic airway are critically dependent on pH in vitro. For example, protonation of nitrite ($NO_2^-$) to form nitrous acid ($HNO_2$;pKa~3.3) and protonation of peroxynitrite ($ONOO^-$) to form peroxynitrous acid ($ONOOH$;pKa~6.3) converts relatively inert salts into highly cytotoxic species. These acids may cause substantial injury to the airway epithelium, largely through the generation of free radicals according to reactions (1) and (2).

$$2H^+ + 2NO_2^- \rightarrow 2HNO_2 \rightarrow H_2O + .NO_2 + .NO \quad (1)$$

$$H^+ + ONOO^- \rightarrow ONOOH \rightarrow .OH + .NO_2 \quad (2)$$

Because of the pH-dependent cytotoxicity of chemical species present in high concentrations in the asthmatic airway, the pH of expired water in subjects with acute asthma was studied. This water was condensed during tidal breathing. Samples were filtered during collection (0.3 µm) and were deareated with argon to eliminate artifact caused by variable carbon dioxide tensions. pH values were highly reproducible and unrelated to salivary pH, to nebulizer therapy or to gastroesophageal reflux history.

The mean pH in subjects with acute asthma was over two log orders lower than in controls (7.65±0.20 vs. 5.23±0.21; n=19 and 22, respectively, p<0.001; representing in excess of 100 fold increase in proton/hydronium ($H_3O^+$) concentration). These findings are consistent with evidence for low nasal epithelial pH in patients with rhinitis and with bronchoalveolar lavage acidification in ovalbumin-sensitized guinea-pigs. Furthermore, endogenous administration of an acid aerosol to human and animal airways is an effective and reproducible method for creating athma symptoms. Specifically, an acid aerosol treatment causes airway smooth muscle constriction and airway epithelial injury, classic features of an acute attack of asthma. Moreover, low airway pH causes the death of inflammatory cells lining the airway with release of toxic mediators that perpetuate inflammation and bronchoconstriction, and likely contributes to elevated levels of nitric oxide found in the exhaled breath of asthmatic patients.

Increased serum and airway ECP levels and increased nitric oxide (NO) production/nitrogen oxide ($NO_x$) toxicity have both been considered markers for worsening asthmatic airway inflammation. These effects of airway acidification thus provide not only a theoretical model explaining cytotoxicity and airflow obstruction in asthma exacerbations, but also describe the specific findings observed during asthma exacerbations in general. Of note, several respiratory epithelial cell functions, such as ciliary motility, are also impaired at low pH, and airway mucous production is increased. It has not previously been suspected that these elements of asthma pathophysiology could be stimulated by endogenous airway acidification.

Endogenous acidification of airway lining fluid may be beneficial during certain infections as an innate host defense mechanism. However, in patients with asthma, this process could be expected to aggravate airway inflammation. Our evidence suggests two important mechanisms by which this acidification selectively affects asthmatic subjects. First, acidification may selectively injure the asthmatic airway through toxification of reactive chemical species. Second, necrosis of resident airway eosinophils caused by a fall in pH will lead release of inflammatory mediators such as eosinophil cationic protein.

SUMMARY OF THE INVENTION

The present invention is based on the premise that endogenous airway acidification, to the degree observed in breath condensates from subjects with acute asthma, is uniquely toxic to the allergic asthmatic airway. An important mechanism by which this acidification occurs involves inhibition of airway epithelial glutaminase by Th1-derived cytokines and by GSNO. Accordingly, based on this discovery, several novel therapeutic strategies for the prevention and treatment of asthma exacerbations can be employed including 1) corticosteroid timing and dosing based on breath condensate pH and/or $NH_4^+$ measurements; 2) inhibition of airway epithelial γGT; 3) identification of novel inducers of glutaminase; 4) dietary or airway supplementation with glutamine during viral respiratory infections for patients with asthma; 5) use of alkalinizing aerosols during asthma exacerbations; and/or 6) aerosolized use of inhibitors of other airway acidification mechanisms, such as of carbonic anhydrase or vacuolar (V) ATPase.

DETAILED DESCRIPTION OF THE INVENTION

In accordance with one embodiment the symptoms of asthma are alleviated by administering a pharmaceutically acceptable basic solution, having a pH of about 7.4 to about 10, to a patient in a form that contacts the airways of the patient. More particularly, the present invention can use any base, delivered by aerosol to the airway, for the purpose of treating asthma. The goal will be to decrease the proton concentration in the airway lining fluid from approximately 10 μM to approximately 100 nM ($10^{-5}/10^{-7}$).

The protons (or $H_3O^+$ ions depending on nomenclature) are buffered to varying degrees in the airways lining fluid, and therefore a molar equivalent of base will not necessarily be sufficient to normalize pH. Instead, an adequate amount of base needs to be provided to the lower airway to react with the protons as they are freed from the airway lining fluid buffer system. This may range from approximately $10^{-5}$ Eq/L in an essentially unbuffered lower airway fluid to $10^{-4}$ in a more highly buffered system. Given that this airway lining fluid is ordinarily approximately 1 ml/kg body weight, this will be approximately $10^{-8}$ to $10^{-7}$ mEq/kg. However, only approximately 10% of an aerosol is effectively delivered to the lower airway. Therefore, the appropriate dose of base would be approximately 0.1 to 1.0 μMole/kg.

Figure 5A:
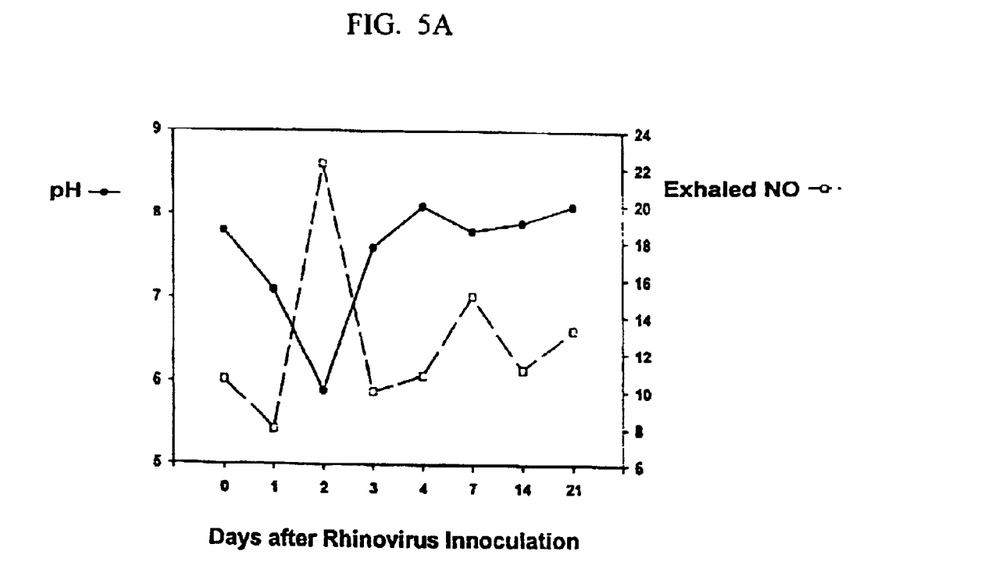
FIGS. 5A and 5B represent a graphic demonstration showing that infection with human rhinovirus causes a fall in pH and increased in expired NO in subjects with asthma who have an IgE>200 IU/mL. Asthmatic (FIG. 5A) and control (FIG. 5B) subjects were innoculated with HRV 16 at time 0. Breath condensate and expired NO was measured at various time points after innoculation. Maximal fall in pH and rise in expired NO occurred 48 hours after innoculation in high-IgE asthma.
Figure 5B:
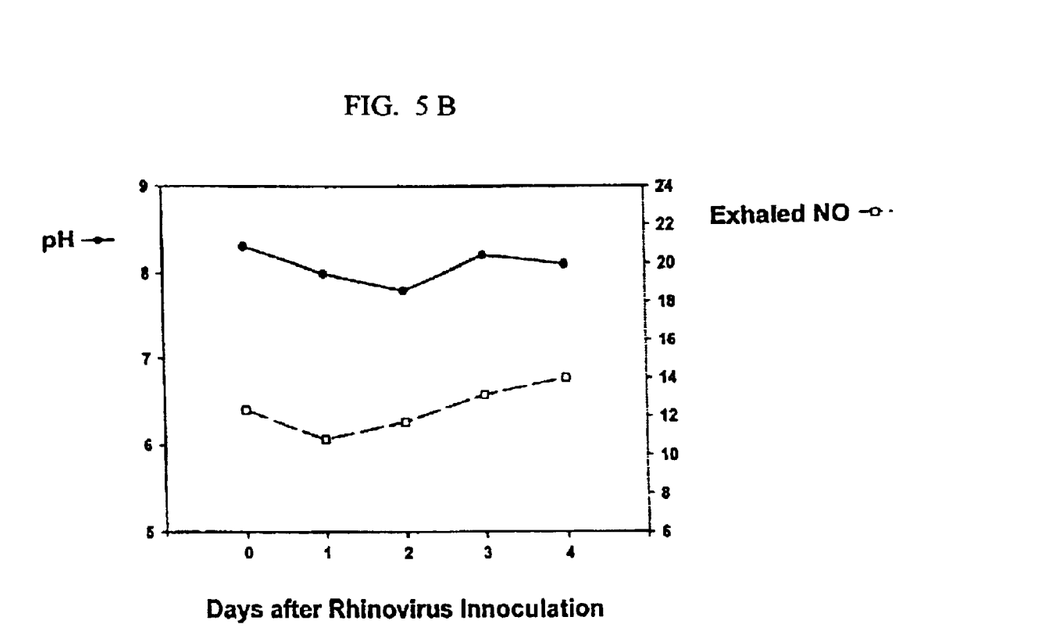

The base used could be an endogenous stable base such as phosphate or an amine, or a synthetic, non-toxic base. In one preferred embodiment the base used is nebulized sodium phosphate monobasic or sodium acetate, or other physiologically acceptable salt of those compounds. The base can be administered alone or in conjunction with glutamine (i.e. administered as a mixture of the base with glutamine or the two components are administered separately but within a short time frame, for example the second being administered within three minutes of the first).

This therapy would be delivered early in the course of an acute asthma exacerbation, when airway pH begins to fall. It would thus prevent the need to use systemic steroids to treat or prophylax against an asthma exacerbation. It could be used in conjunction with measurement of airway pH by condensation technique: That is, the use of base could be judged, and the dose of base titrated, according to the endogenous airway pH as measured by condensation technique using techniques known to those skilled in the art. This would allow for precise and "natural," nontoxic therapy for asthma exacerbations.

The idea of using natural compounds and adjusting therapy according to endogenous pathologic response is likely to have tremendous appeal to patients adverse to using pharmacologic agents for asthma management, and is likely to not have the toxicities associated with corticosteroids anti-inflammatory therapy and β-agonist smooth muscle relaxants.

In another embodiment of the present invention, alkaline buffer systems can be delivered to the airway. Such systems would include, but not be limited to, combinations of ammonia ($NH_3$) and conjugate acids of $NH_3$ such as ammonium acetate, ammonium chloride, or ammonium bicarbonate, in a system with concentrations of base/conjugate acid and added salts (such as sodium chloride) such that the pH, $pK_a$, buffer capacity, and ionic strength of the fluid are best suited to use for treatment of various levels of acidity in the asthmatic airway. Additionally, other basic buffer systems could be used, such as, but not limited to, glycine (aminoacetic acid), $pK_a2$=9.78), bicine (N,N-Bis(2-hydroxyethyl)glycine ($pK_a$=8.46), tricene (N-[tris (hydroxymethyl)methyl] glycine $pK_a$=8.26), CAPS(3-(Cyclohexamino)-1-propanesulphonic acid (10.51), CAPSO (3-(Cyclohexamino)-2-hydroxypropanesulphonic acid ($pK_a$=9.71), 2-(Cyclohexamino)-ethenesulphonic acid ($pK_a$=9.41), to name a few. The choice of buffer system could also be individualized for patients depending on results of non-invasive measurements of airway redox chemistry (based on airway vapor condensate assays).

In an alternative embodiment of the present invention, pharmacologic agents are administered to an asthmatic that prevent the production of acid in the airway, and/or enhance the production of base in the airway endogenously, as a treatment for asthma. We have also discovered that mean breath condensate concentrations of acetic acid in subjects with acute asthma (9.5 mg/L; n=9) are over 4 times higher than those in controls (1.76 mg/L; n=18), in part explaining the lower pH in the asthmatic samples. Decreasing acetic acid production would therefore be an effective treatment for asthma. For example, a patient can be treated with a nebulized formulation or treated systemically with a compound that inhibits aldehyde dehydrogenase (such as Disulfiram), to prevent formation of acetic acid in the lung. Alternatively, or in addition to other therapies, a patient can be treated with a nebulized formulation or treated systemically with antifungal agents such as fluconazole, which kills yeast that may ferment sugars and provide substrate for acetic acid formation in the lung.

The airway epithelial surface can maintain a constant pH at differing levels of $pCO_2$, and this homeostasis has been attributed to a variety of epithelial cell functions including carbonic anhydrase activity, basolateral $Na^+/H^+$ exchange and lumenal $HCO_3^-$ exchange through Cl channels. However, applicants have discovered an additional mechanism by which airway pH may be regulated, involving the production of $NH_3$ by glutaminase in human airway epithelial cells. Robust mRNA and protein expression for the human kidney (hKGA) and human C (hGAC) isoforms of glutaminase are evident in human lower airway epithelial cell populations. Therefore one aspect of the present invention is based on the principle that glutaminase-derived $NH_3$ buffers acid in the airway (as it does in the kidney) by forming airway lumenal $NH_4^+$. In addition applicants have shown that $NH_4^+$ concentrations are low in the expired air condensates of patients with acute asthma who have low pH (median: range=37; 0–442 microM; n=23) compared to controls (314: 14–1220 microM; n=16; p<0.001). Thus in accordance with one embodiment, asthma can be treated by administering aerosolized glutamine.

Glutaminase activity increases in the renal tubular epithelium to compensate for epithelial acidification. Expression is also strongly upregulated by corticosteroids and inhibited by certain inflammatory cytokines. Compensatory stabilization of glutaminase mRNA in response to an environmental acid load has recently been demonstrated to involve binding of a cytoplasmic protein to an eight-base AU repeat. The only known promoter for the glutaminase gene is dexamethasone-responsive, consistent with observations that corticosteroid treatment increases airway pH in asthmatic subjects suffering from an acute exacerbation (see FIG. 5). Moreover, glutaminase expression is consistently inhibited by interferon γ (IFN γ) in the kidney and airway.

In accordance with one embodiment of the present invention a method for treating asthma comprises administering a pharmaceutically acceptable compound that either directly or indirectly raises the pH of the bronchial airways. As used herein the term treating includes alleviating the symptoms associated with a specific disorder or condition and/or preventing or eliminating said symptoms. Examples would include, but not be limited to, inhibition of airway V ATP'ases (which produce acid) and stimulation of airway epithelial glutaminase (which can produce base). The activity of glutaminase is inhibited by Th1 cytokines and is upregulated by corticosteroid therapy. Agents that inhibit airway acid production can be delivered either by aerosol or systemically in oral parenteral form. In one embodiment the therapy would also include providing a substrate to glutaminase (specifically glutamine) and other enzymes capable of producing ammonia (a base produced endogenously in the airway).

The present disclosure also encompasses the use of conventional agents such as Albuterol or Ipratroprium, currently used in day-to-day practice of asthma management, at more alkaline pH. Existing formulations are administered a an acidic pH:

Albuterol, pH 3 to 5

Levalbuterol HCl, pH 3.3–4.5

Ipratroprium bromide, pH 3–4

In accordance with one embodiment of the present invention an improved nebulizer solution is provided wherein the pH of existing formulations are modified to have a pH of greater than 7, and more preferably a pH of about 7.5 to about 9.5. This would involve alkalinization of the medicine immediately prior to use by mixing in a preformed diluent (phophate buffer pretitrated to the acidity of the medicine, for example) as opposed to normal saline. It also embodies the mixture of these conventional agents in an alkaline buffer system capable of neutralizing airway acids. In one embodiment these standard compositions can be combined with glutamine to supply a substrate for glutaminase and thus further alkalinate the bronchial airways.

In one embodiment, a kit is provided for treating asthma. The kit comprises a conventional asthma compound, for example albuterol, levalbuterol HCl, ipratroprium bromide, or budesonide in solution, and a buffered diluent, wherein the diluent will effectively raise the pH of the solution to a basic pH. Suitable buffers are well known to those skilled in the art and a buffer can be selected that does not interfere with the activity of the conventional asthma agent.

In accordance with the present invention, asthmatic patients can be treated by lowering the pH of fluids that asthmatic contact during an ordinary day. For example, the present invention also includes the use of alkaline humidification of the air for treatment and prevention of asthma exacerbations. Furthermore, household water can be alkalinized (with such agents as soda ash) and used for the specific purpose of treating asthma or airway diseases associated with an acidic airway lining fluid. In one embodiment, part of the therapy for treating asthma prophylactically comprises the use of environmental filters to scrub protons (acid rains and acid fogs) that may aggravate endogenous airway acidification during conditions of atmospheric pollution, thus worsening or predisposing to an asthma exacerbation.

This disclosure also encompasses the use of methods described in the above paragraphs in conjunction with traditional methods of asthma management. Further, it claims the use of normalization of airway pH as a measure of efficacy by which to titrate the use of conventional asthma therapies, such as systemic and inhaled glucocorticoids. The use of glucocoticoids for treatment of asthma is consistent the fact that the only known promoter for the glutaminase gene is dexamethasoneresponsive, and that corticosteroid treatment increases airway pH in asthmatic subjects suffering from an acute exacerbation. Therefore the effect of glucocoticoid treatment may be mediated through the stimulation of glutaminase expression. The dose of oral glucocorticoids (Prednisone, for example) a patient may take may be tapered or discontinued once the airway pH is normalized. This therapy could be used to decrease the level of intervention for patients with severe asthma who are chronically on relatively high doses of glucocorticoids. In this embodiment, daily or repeated daily use of an aerosolized base would be used to decrease the dose of potentially more toxic compounds required to keep the patient asymptomatic. One compound suitable for use in accordance with the present invention is aerosolized glutamine.

The methods described above can also be used to modify the pH of the nasal fluids, particularly in regards to treatment of symptoms and underlying mechanisms of pathology for allergic rhinitis and common cold viruses such as rhinovirus and other airway based infections. Both allergic rhinitis and common cold viruses likely decrease the pH of nasal secretions, with various toxicities thereby resulting. In particular, viral infections, by stimulating a Th1 and/or CD8 lymphocyte response, may initiate the airway acidification that ultimately contributes to asthma symptoms, and thus modifying the pH of the patients airways may alleviate symptoms associated with such infections.

Human Rhinovirus (HRV) infections are a leading cause of acute asthma exacerbations in children over two, as well as in adults. The mechanism by which HRV selectively initiates expiratory airflow obstruction in patients with asthma is not completely understood, however airway pH homeostasis may play an important role. Acute asthma exacerbations commonly follow HRV infections. Applicants have recently demonstrated that breath condensate pH and $NH_4^+$ levels fall dramatically and in parallel with a fall in condensate ammonum levels from a median of 351 (range 152–1585) microM to 65 (4–713) microM p<0.05 in asthmatic subjects experimentally inoculated with HRV strain 16 in human subjects approximately 72 hours following experimental HRV 16 infection (see FIGS. 5A and 5B). Because this fall in pH could lead to asthma symptoms in patients with eosinophilic airway inflammation and high levels of $NO_x$, this drop in pH likely contributes to lower airway symptoms in asthmatic patients who develop an upper respiratory infection. Rhinovirus infection could lead to inhibition of glutaminase and a fall in lung water pH by several mechanisms, including, 1) direct infection of lower airway respiratory epithelial cells; 2) a cytokine-mediated inflammatory response; and/or 3) a neural signaling pathway.

Direct infection of the lower airway with HRV during acute asthma exacerbations has been postulated. However, the role of glutaminase in direct infection has not been described, and the direct effects of HRV infection alone on airway epithelial cells (in the absence of an immune response) are subtle. The role of glutaminase in human rhinovirus (HRV)-exacerbated asthmatic airway disease relates to its ability to modulate airway pH. Acidification of the airway is cytotoxic and contributes to asthmatic airway disease by 1) protonating nitrite ($NO_2^-$) and peroxynitrite ($ONOO^-$) to form membrane-destructive species such as hydroxyl (.OH) and nitrogen dioxide (.$NO_2$) as well as nitric oxide (.NO); 2) eosinophil necrosis; 3) increased mucous secretion and 4) impaired ciliary beating. Airway acid is buffered by ammonia ($NH_3$) evolved from glutaminase-derived ammonium ($NH_4^+$) with basolateral loss of $H^+$ in exchange for $Na^+$.

An indirect effect of HRV infection involving inflammatory and/or neuronal mediators is also possible. In particular, IFN γ is a likely candidate to mediate glutaminase inhibition because 1) Th1 cytokines inhibit glutaminase activity in lower airway epithelial cells 2) IFN γ inhibits glutaminase in other cell systems; and 3) IFN γ production following HRV infection in the setting of Th2-lymphocyte associated chronic inflammation may contribute to asthmatic airway narrowing. Applicants have shown that 100 u/ml interferon gamma inhibits glutaminase activity in cultured lung epithelial cells in excess of 65% at 24 and 48 hours (p<0.01, N=3 each). Though circulating T cells could produce IFN γ during rhinovirus infections, it seems more likely that it would be secreted in the airway itself as a result of local recruitment and activation of Th1 and/or CD8 cells.

Applicants have shown that a class of endogenous neuroregulatory molecules known as S-nitrosothiols also inhibit glutaminase activity 100% at 24 hours (p<0.01, n=3), probably through S-nitrosylation of a critical cysteine on the enzyme. In accordance with one embodiment, a method of treating asthma comprises nebulizing or treating systemically with a compound that facilitates breakdown of S-Nitrosothiols, such as CuCl, Cu/Zn SOD, glutathione peroxidase, glutathione-dependent formaldehyde dehydrogenase or gamma glutamyl transpeptidase. The presence of S-nitrosothiols in the airways may be derived from airway epithelial cells themselves during Th1-stimulated nitric oxide synthase 2 upregulation, perhaps providing a cellular mechanism by which IFN γ inhibits glutaminase. IFN γ's role in inhibiting glutaminase may offer yet another means of treating asthma that can be used alone or in conjuctions with the other methodologies of the present invention. In one embodiment, an asthmatic patient can be treated with a Nebulized formulation or treated systemically with an antibody to interferon gamma.

Additionally, the presence of S-nitrosothiols in the airways may arise from other inflammatory cells in the airway and/or from non-adrenergic, non-cholinergic nerves in the airway wall. Of note, though SNOs tend to be catabolized rapidly in the airway lumen of asthmatic humans and ovalbumin sensitized guinea pigs, a critical catabolic enzyme, γ glutamyl transpeptidase (GGT), bioactivates the most common of these SNOs, S-nitrosoglutathione (GSNO), forming the cell-permeable product, S-nitrosocyteinyl glycine (CGSNO). This pathway from GSNO to the bioactive S-nitrosylating agent CGSNO is relevant both in the nervous system and in the lung, and may be involved in signaling the inhibition of glutaminase during HRV infections.

Taken together, these observations suggest that HRV causes lung water pH and $NH_4^+$ levels to fall through inhibition of glutaminase, whether through direct infection of the lower airway cells, through lymphocyte-mediated pathways and/or through neural activation. Accordingly, methods that counteract the inhibitory effect on glutaminase, or raise airway pH may be effective in treating HRV infections-induced asthma exacerbations.

In another embodiment of the present invention airway acidosis mediated through protonation reactions involving reactive nitrogen and oxygen species may have antimicrobial effects. In particular nitrite acidification has been proposed as a mammalian host defense mechanism. The abundant $NO_2^-$ of the airway is present as bacteriotoxic $HNO_2$ in relevant quantities only when the pH is low. *Mycobacterium tuberculosis* produces a gene product specifically protecting against the effects of $HNO_2$. Some of the toxicity of $HNO_2$ occurs because of its reactive decomposition to NO, which is known to inhibit mycobacterial growth. Additionally, hydrogen peroxide, elevated in the condensed breath of asthmatic patients, acts synergistically with $HNO_2$ to kill gram negative, mycobacterial and viral organisms. Applicants believe this to be the reason that the human organism has adopted the mechanisms we have discovered to acidify lung water. For example, as is shown herein, lung water pH and ammonium level fall in response to HRV infection (see FIGS. 5A and 5B). As such, restoration and/or augmentation of the acidifying mechanisms of the airway (and mechanisms to deprive invading micro-organisms of ammonia) will be effective treatments for lung infections, such as tuberculosis. A decline in airway pH would also favor protonation of the relatively stable NO-superoxide reaction product, peroxynitrite ($OONO^-$) to peroxynitrous acid (OONOH), anoxidizing and nitrating species involved in macrophage-mediated mycoplasma killing. These observations suggest that mild airway acidification may be a subtle and titratable innate host defense mechanism which takes advantage of the pKa's of weak endogenous acids to defend the airway against airborne pathogens.

In accordance with one embodiment a method of treating microbial infections of the airways comprises administering a composition that results in the acidification of the airways. In preferred embodiments the composition is deliver as an aerosol. In one embodiment the composition for lowering the pH of the airways comprises a proton donor, for example acetic acid, phosphoric acid, or dilute hydrochloric acid, or other proton donors. Alternatively, the composition may comprise S-nitrosothiols, such as S-nitrosoglutathione or S-Nitroso-N-acetyl cysteine, not to kill the organism directly, but to inhibit glutaminase. In addition, the composition may comprise nebulized Diazo-5-oxo-L-norleucine, an inhibitor of glutaminase. In accordance with one embodiment a method for treating a *Mycobacterium tuberculosis* infection comprises inhalation of a composition that lowers the pH of the airways to a range of about 6.0 to about 6.9.

EXAMPLE 1

Data Supporting the Hypothesis That Airway Acidification Contributes to the Pathophysiology of Acute Asthma.

Eosinophil Necrosis and Release of Cytotoxic Mediators is Enhanced in Allergic Asthmatic Subjects by Endogenous Airway Acidification During Viral Respiratory Infections.

Consistent with the established cellular toxicity of low pH-mediated protonation of $NO_x$, applicants have recently described that human eosinophil necrosis (and overall cell death) are dramatically accelerated in the upper end of the pH range observed during acute asthma exacerbations compared to that observed in asymptomatic controls (Am J Respir Crit Care Med 161:694–699;2000). Further breath condensate pH falls during HRV 16 infection. This drop in pH affects both the upper and lower airways. Direct measurement of nasal lavage pH (though diluted by saline) in high IgE asthmatic and control subjects infected with HRV16 (n=3 each) revealed that the asthmatic subjects had high ECP levels (258–668 ng/ml) associated with low pH (mean 6.9) while controls had low ECP levels (8–77 ng/ml) associated with normal pH (7.5). These results are consistent with overall results showing that HRV 16 infection causes an increase in nasal ECP levels selectively in the high IgE-asthmatic group.

Figure 4:
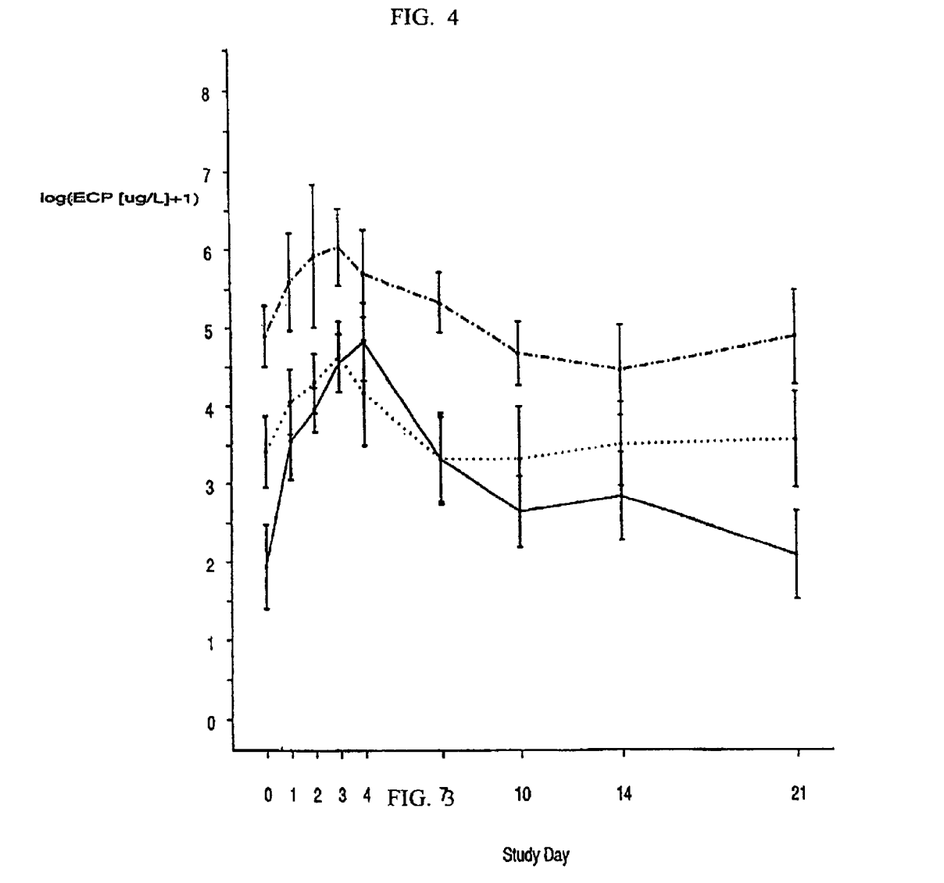
FIG. 4 is a graphic demonstration showing that experimental HRV 16 infection is associated with increased upper airway ECP levels. Ten non-allergic, non-asthmatic subjects (—), 11 subjects with asthma and relatively low IgE values (29.2–124 IU/mL) (•••••) and six subjects with high IgE values (371–820 IU/mL) and asthma (-•-•-•-) were innoculated intranasally with HRV 16,500 tissue culture infective dose 50% ($TCID_{50}$)/mL, 2.5 mL in each nostril twice at time 0. Nasal lavage ECP levels were measured sequentially for three weeks.

Experimental HRV 16 infection is associated with increased upper airway ECP levels. Ten non-allergic, non-asthmatic subjects, 11 subjects with asthma and relatively low IgE values (29.2–124 IU/mL) and six subjects with high IgE values (371–820 IU/mL) and asthma were innoculated intranasally with HRV 16 (500 tissue culture infective dose 50% ($TCID_{50}$)/mL, 2.5 mL in each nostril twice at time 0. Nasal lavage ECP levels were measured sequentially for three weeks (See FIG. 4). All groups experienced an increase in upper airway ECP levels on the day after experiencing a fall in pH. Indeed, most subjects experience some degree of fall in airway pH with inflammation. However, the rise in ECP was substantially more pronounced in the high IgE-asthamatic group (p<) than in controls or lower-IgE asthamtics. This difference may be multifactorial, but suggest that the allergic asthmatic response to airway acidification may involve increased release of inflammatory mediators.

The Cytotoxicity of Nitrogen Oxides Present in High Concentrations in the Asthmatic Airway is Enhanced by a Fall in Lung Water pH.

Nitrogen oxide ($NO_x$) levels are elevated in the lower airway and breath condensates of patients with asthma. It has been previously reported that asthma is associated with high breath condensate nitrite ($NO_2^-$) and expired NO levels, consistent with evidence that nitric oxide synthase Type 2 (NOS 2) is chronically upregulated in the asthmatic lung. More recently, direct bronchoscopic evidence has been obtained that nitrogen oxides ($NO_x$) (including the peroxynitrite ($ONOO^-$) rearrangement product nitrate) tend to be elevated in the lower airways of subjects with mild asthma ($3\pm1$ $\mu M$[n=8] vs. $1.7\pm0.3\mu M$ in controls[n=8]; p=0.06) and are increased in asthmatics relative to controls 48 hours after segmental antigen challenge (to $6\pm1$ $\mu M$ vs $1.6\pm0.4$ $\mu M$; p=0.02).

When exposed to acid, the airway $NO_x$ present in high concentrations in the baseline or antigen-challenged airway will be protonated, forming ONOOH (pKa~6.8) and $HNO_2$ (pKa~3.4), compounds each substantially more cytotoxic than the corresponding base. Tissue injury caused by the protonated species is mediated, at least in part, by disproportionating reactions that form radical species including OH (from ONOOH), $.NO_2$ (from ONOOH and $HNO_2$) and .NO (from $HNO_2$) (Reactions 1 and 2). Consistent with data from other groups suggesting accelerated ONOOH formation in the asthmatic airway, applicants have recently shown that reaction (1) proceeds rapidly during endogenous acidification of the asthmatic airway, consuming $NO_2^-$ and producing NO (Am J Respir Crit Care Med 161:694–699;2000). We have also shown that inhalation of an alkaline aerosol (0.05 mL/kg of 10 mM phosphate buffered saline [PBS]) in acute asthma reverses this process, decreasing expired NO levels. Because there is now substantial evidence that expired NO values collected according to ATS guidelines reflect lower airway (rather than nasal) NO evolution, this experiment also provides indirect evidence suggesting that pH measurements made on breath condensate specimens reflect lower airway chemistry.

EXAMPLE 2

Data Supporting the Hypothesis That Airway Acid is Buffered by Ammonia, a Product of Epithelial Glutaminase.

Ammonium Concentrations are Low in Breath Condensate Specimens From Patients with Acute Asthma.

Figure 1:
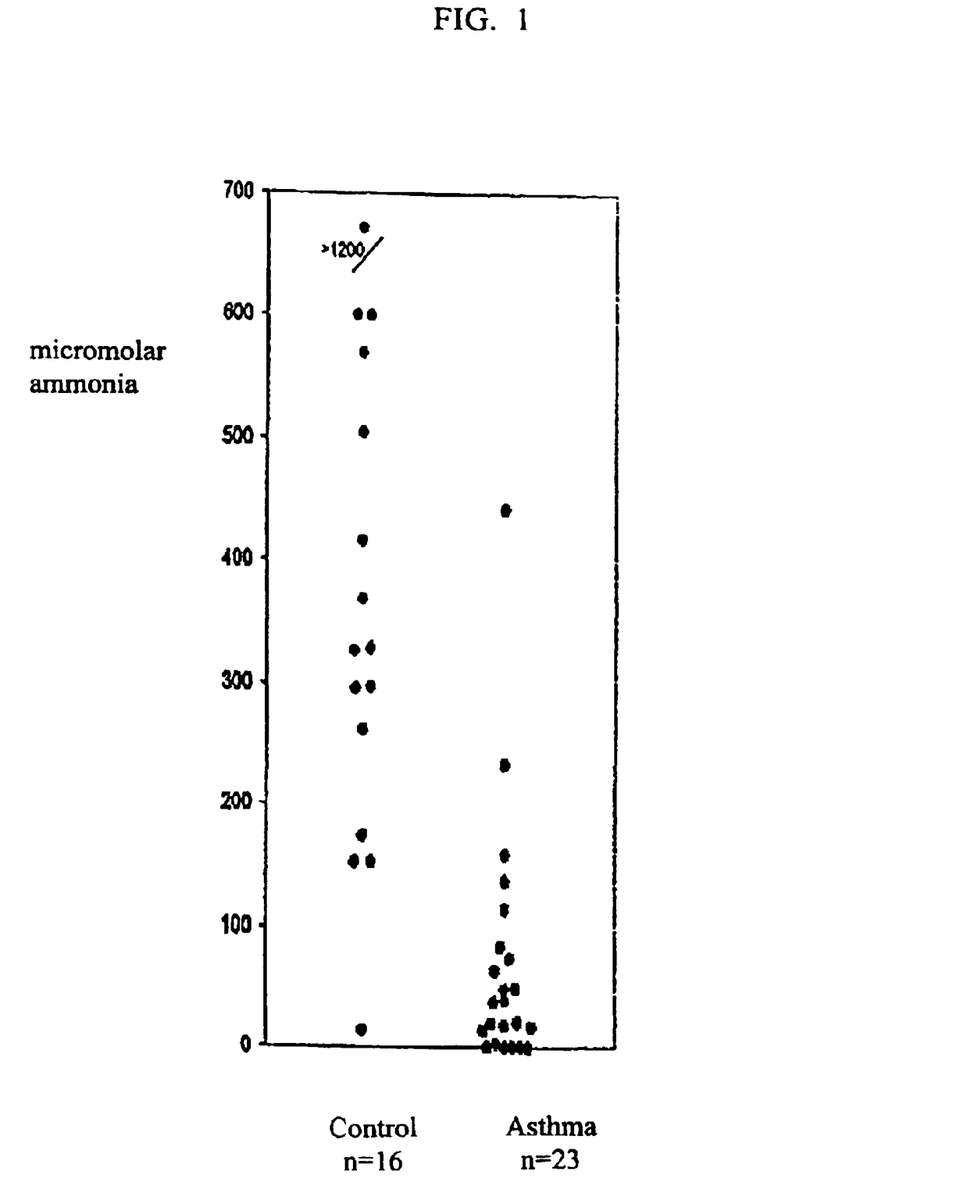
FIG. 1 is a graph showing ammonium concentrations are low in breath condensate specimens from patients with acute asthma. Specimens were collected from patients admitted to the hospital or seen in the emergency department with acute exacerbations of asthma (low pH) or from healthy volunteers. The median $NH_4^+$ concentration in asthmatic subjects (37; range, 0–442) was lower than in controls (314; range, 14–220) by Mann-Whitney rank-sum testing (p<0.001).
Figure 2:
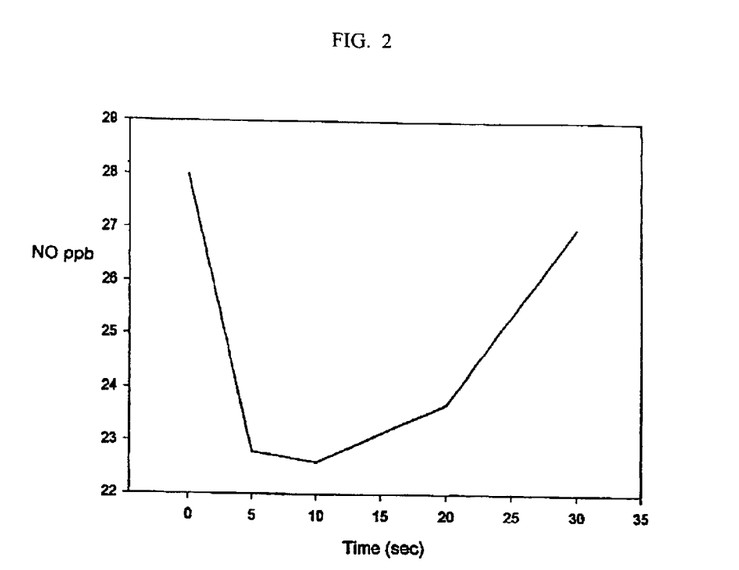
FIG. 2 is a graphic demonstration showing that inhalation of phosphate-buffered saline decreases expired NO concentration in asthma. Nebulized treatment with 0.05 mL/kg 10 mM PBS at time 0 results in a time-dependent decrease in expired NO concentration in acute asthma.
Figure 3:
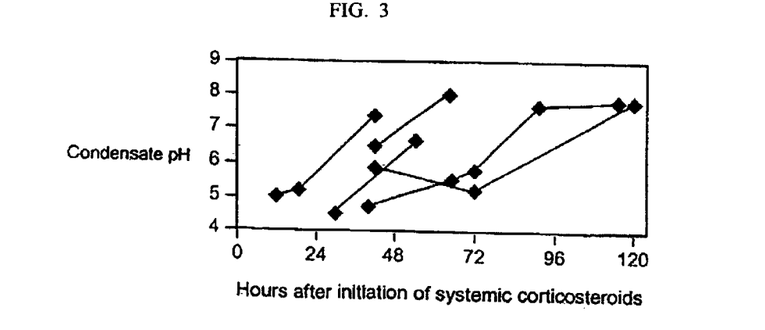
FIG. 3 is a graphic demonstration showing that breath condensate pH normalizes during corticosteroid treatment for acute asthma. Serial pH measurements were made on five hospitalized patients with asthma and receiving corticosteroid treatment. Geometric mean pH after treatment (7.5±0.23) was over two logs than at the intitiation of treatment (5.3±0.38; p=0.001).

Specimens were collected from patients admitted to the hospital or seen in the emergency department with acute exacerbations of asthma (low pH) or from healthy volunteers (no history of asthma or any other obstructive lung disease and no chronic or acute illness). All patients with asthma had acute expiratory flow limitation, with auscultatory wheezing, an inspiratory to expiratory time ratio of $<\frac{1}{2}$, and/or peak expiratory flow or forced expiratory volume at one second ($FEV_1$) values <80% of predicted. The median $NH_4^+$ concentration in asthmatic subjects (37; range, 0–442) was lower than in controls (314; range, 14–220) by Mann-Whitney rank-sum testing (p<0.001). Logarithmically-transformed $NH_4^+$ concentrations were correlated with logarithmically-transformed $H^+$ concentrations (pH) (r=0.59; p<0.001). Thus subjects with acute asthma exacerbations who have a low breath condensate pH also have low breath condensate $NH_4^+$ levels (see FIG. 1).

Glutaminase Protein is Expressed in Human Airway Epithelial Cells.

Human kidney (KGA) and C-type (GAC) glutaminase transcripts are present in human airway epithelial cells. Total RNA was isolated from confluent normal human bronchial epithelial cells (NHBE; Clonetics) harvested by trysinization. $10^7$ cell aliquots disrupted in lysis buffer (1% β-mercaptoethanol and guanidine isothiocyanate) and homogenized using QIA shredder spin columns (Qiagen, Valencia, Calif.). Lysate was treated with 70% ethanol (1:1 v:v), applied to a RNeasy mini spin column (Qiagen), washed, eluted by centrifugation (10,000 g; 1 min) in 30 $\mu L$ deioinized water and quantified by spectrophotometry. Aliquots of RNA were mixed with KGA or GAC specific upstream and downstream or nested downstream primers and deoxynucleotides in RT-PCR buffer (ProStar HF single-tube RT-PCR system, Stratagene, La Jolla Calif.). Primers were constructed according to Elgadi, et al., (Physiol Genomics 1:51–62; 1999). Moloney murine leukemia virus reverse transcriptase was added to each reaction, with the exception of control reactions used to evaluate for DNA contamination of the isolated RNA. In a control reaction, standard primers for the housekeeping gene glutaraldehyde phosphate dehydrogenase (GAPDH) were used. 0.5 $\mu l$ of TaqPlus Precision DNA polymerase was added next. The reaction mixtures were placed in a thermal cycler and subjected PCR amplification. The PCR products were analyzed by ethidium bromide stained 1% agarose gel electrophoresis in comparison to a 100 bp DNA ladder (GIBCO BRL, Grand Island, N.Y.). The predicted products were identified.

Glutaminase protein is expressed in human airway epithelial cells and is upregulated by corticosteroids in vivo. Open lung biopsy specimens from a subject with histologically normal lung who had been treated with systemic corticosteroids for a month were compared with those from a subject with a severe asthma exacerbation who had been treated with systemic corticosteroids for one day. Tissues were immunostained simultaneously and identically. Briefly, 3–5 $\mu m$ formalin-fixed sections were deparaffinized and rehydrated with decreasing gradients of xylose and of ethanol. Endogenous peroxidase activity was removed by incubation in 3% peroxide. Sections were blocked with normal serum and incubated overnight (4° C.) with or without a polyclonal antibody to glutaminase (KGA). After washing, sections were incubated with or without (one section each with only primary and only secondary antibody) goat-anti rabbit biotinylated secondary antibody, followed by incubation with ABC (avidin-biotinylated horseradish peroxidase macromolecular complex) solution. Glutaminase staining was visualized using 3 3' diaminobenzidine substrate (Sigma). Sections were counterstained briefly with hematoxylin, dehydrated, and mounted using Permount. More glutaminase immunoreactivity (brown) in the airway epithelium of the control subject was observed than of the asthmatic subject and the same was true of the alveolar epithelium. The secondary antibody in the absence of primary antibody (control) had no reactivity; and the same was true using primary antibody and no secondary antibody for both tissues.

Experimental HRV 16 Causes a Fall in Breath Condensate $NH_4^+$ Concentration as Well as a Fall in Breath Condensate pH.

Consistent with observations made during acute asthma exacerbations, breath condensate $NH_4^+$ concentrations fell from a median of 351 $\mu M$ (range 151–1585) to 65 $\mu M$ (range, 4–713; $p<0.05$) following experimental HRV 16 innoculation. Additionally, breath condensate pH fell.

Th-1 Lymphocyte-Derived Cytokines Inhibit Airway Epithelial Glutaminase.

Acute infection with HRV may activate and/or recruited Th1 lymphocytes to the airway and may increase circulating and airway levels of IFN $\gamma$, which may worsen asthma symptoms. Th1-derived IFN $\gamma$, in turn, is known to inhibit glutaminase in human fibroblasts and in airway epithelial cells. Therefore, HRV 16 may acidify lung water in part through the effect of IFN $\gamma$ on glutaminase.

S-Nitrosothiols Inhibit Airway Epithelial Glutaminase.

S-Nitrosoglutathione (GSNO) is an endogenous neuroeffector and immune modulatory molecule that is formed during NOS activation in neuronal and inflammatory cells. There is evidence that it is an important modulatory compound in non-adrenergic, non-cholinergic autonomic signaling. A proposed mechanism by which upper airway HRV infection may signal lower airway symptoms in patients with asthma involves autonomic signaling pathways, and GSNO is a signaling candidate.

GSNO has been demonstrated to inhibit airway epithelial glutaminase activity: Small airway epithelial cells (SAEC: Clonetics) grown to confluence in six well plates with 3 mM glutamine were incubated with S-Nitrosoglutathione (GSNO; 200 $\mu M$) in the presence or absence of cysteinyl glycine (CG; 100 $\mu M$). Ammonium accumulation over time was compared with control cells. S-Nitrosoglutathione require conversion to S-Nitrosocysteinyl glycine (CGSNO) (whether through simple transnitrosation reactions in the presence of CG or through cleavage by $\gamma$ glutamyl transpeptidase) to be fully active at intracellular sites, such as mitochondrial glutaminase, in some sytems. However, conversion of GSNO to CGSNO dramatically shortens the chemical and biological half-life of the SNO moiety. In this experiment, GSNO inhibited $NH_4^+$ accumulation at each time point ($p<0.01$ by ANOVA), an effect that was augmented at 24 hours by CG ($p<0.01$ compared with GSNO; no $NH_4^+$ at all accumulated). As expected, addition of CG eliminated the GSNO effect after 48 hours because it accelerated catabolism. Accumulation of $NH_4^+$ in medium alone was at the threshold of detection. S-Nitrosothiols did not affect cell viability as assessed by trypan blue/light microscopy.

Inhibition of airway epithelial glutaminase is likely to be the result of post-translational interaction of the S-nitrosothiol with the critical catalytic cysteine of glutaminase, consistent with similar mechanisms of regulation described for a large repertoire of other proteins. Of note, it has been shown that NOS activation in airway epithelial cells themselves may result from HRV-initiated IFN $\gamma$ signaling, suggesting that S-nitrosylation may itself be the downstream biochemical mechanism by which IFN $\gamma$ inhibits glutaminase. Importantly, it has also been shown that activation of GSNO by $\gamma$ glutamyl transpeptidase ($\gamma$GT) to S-Nitrosocyteinyl glycine is essential for many of its bioactivities and also is involved in GSNO catabolism. Therefore, increased airway $\gamma$GT evident during acute asthma exacerbations could also account, at least in part, both for accelerated GSNO catabolism and for inhibition of airway epithelial glutaminase.

EXAMPLE 3

Determining Airway Acidification Contributes to the Pathophysiology of Acute Asthma Methods Ammonium Measurement Concentrations will be determined by the Sigma Diagnostics method. Briefly, condensed exhaled airway fluid vapor and supernatant from native tracheobronchial secretions will be reacted with NADPH in the presence of L-glutamate dehydrogenase which reductively aminates added 2-oxoglutarate. The decrease in absorbance at 340 nm reflects NADPH oxidation and is proportional to NH3 concentration.

Breath Condensate 3NT Measurements.

These will be performed as reported by Hanazawa and coworkers (Am J Respir Crit Care Med 162:1273–1276, 2000). Subjects will breathe through a mouthpiece and a two-way nonrebreathing valve which also serves as a saliva trap. Nitrotyrosine will be measured with a specific enzyme immunoassay according to the manufacturer's indtructions (Cayman Chemical, Ann Arbor, Mich.).

Bronchial Epithelial Biopsy.

Following administration of topical lidocaine anesthesia, forceps will be opened and advanced on the membranous side of the main, left and right carinae, closed and removed. Specimens will be placed initially in saline, and considered adequate if there is minor erythema and/or bleeding at the biopsy site, and if an inhomogeneous tissue sample at least 1 mm in width is visualized in the saline. If the sample is inadequate, the site will be re-biopsied.

Bronchoscopic Airway pH Measurement.

Filter paper will be cut from Whatman 541 hardened ashless paper (Clifton, N.J.). Individual papers for the nasal studies were to 4 mm by 1 cm, washed in double-distilled, deionized water and dried in an oven overnight. pH neutralizing of the paper batch will be confirmed by placing deionized water on the paper and reading the pH from a Cardy micro pH meter. Papers were folded in half widthwise, and weighed on the day used (just before sampling). The end of the paper was grasped in the forceps and positioned on the epithelial surface for 20 seconds. The pH will be measured (Cardy) immediately after removing the forceps. Three measurements will be made on each subject.

Epithelial HRV 16 Infection.

Stocks of HRV16 from Dr. Hayden's laboratory will be grown in confluent HeLa Ohio cells in minimal essential medium. Tissue culture infective dose 50% ($TCID_{50}$) will be determined by viral titration in 96-well plates of HeLa cells cultured for 5 days and evaluated for cytopathic effect by fixation in methanol and staining with 0.1% crystal violet. Aliquots of HRV 16 will be inactivated with 1200 $\mu J/cm^2$ uv light for 30 min. Medium will be removed from epithelial cells grown to confluence in 6-well plates and cells will be infected using 1 mL aliquots of active or uv-inactivated HRV 16 for 8, 24, 48 and 72 hrs. Cells will be assayed for glutaminase expression and activity at each time point.

Glutaminase Immunoprecipitation.

Cells will be lysed in 1 mL NP-40 buffer (150 mM NaCl, 1% NP-40, 50 mM TRIS, pH 8.0) containing protease inhibitors for 30 min (4° C.). The Lysate will undergo centrifugation (16,000 rpm; 10 min; 4° C.). The lysate will be precleared of proteins which bind nonspecifically to antibody and protein A beads during a 2 hr incubation at 4° C. with 25 mL protein A beads which have been preincubated with irrelevant antibody. The beads will be removed after a 5 second centrifugation and the cleared supernatant will be incubated with 5 mg/250 mg protein anti-rat kidney polyclonal antibody (or 20 mg/mL IgG as control) overnight, then with 50 mL pre-quilibrated protein A beads for two hrs (each at 4° C.). Immunoprecipitates will be collected at 2,500 rpm (5 min, 4° C.) and Washed five times in 500 mM NaCl, 1% NP-40, 50 mM TRIS, pH 8.

Immunoperoxidase Staining.

This will be performed using VECTASTAIN Elite kit (Vector Laboratories) as described by the manufacturer. Briefly, serial sections of formalin-fixed paraffin-embedded lung will be mounted on precleaned Superfrost Plus slides (Fisher Scientific). Tissue sections (3–5 µm) will be deparaffinize and rehydrated with a decreasing gradient of ethanol. Endogenous peroxidase activity will be removed by incubation in 3% peroxide. Tissue sections will be blocked with normal serum and incubated overnight at 4° C. with a polyclonal antibody for glutaminase (courteously supplied by Dr. Norman Curthoys). After washing to remove unbound antibody, sections will be incubated with goat-anti rabbit biotinylated secondary antibody followed by incubation with ABC (avidin-biotinylated horseradish peroxidase macromolecular complex) solution. Controls will includereaction with primary antibody only, secondary antibody only and primary antibody pre-incubated with excess glutaminase. Glutaminase staining will be visualized using 3, 3'diaminobenzidine substrate (Sigma). Sections will be counterstained briefly with hematoxylin, dehydrated, and mounted using Permount.

In situ Hybridization (ISH).

This will be performed in lung tissue in order to identify the precise location and identification of cells containing glutaminase transcripts. In these studies, ISH will be performed on serial sections of formalin-fixed paraffin-embedded lung mounted on 2-aminopropyltriethoxysilan coated slides. Two plasmids will be constructed: (1) pBS480GAC which contains 480 bp of the GAC gene and (2) pBS640KGA which contains 640 bp of the KGA gene. Plasmids will be linearized and sense and antisense riboprobes transcribed using T7 or T3 RNA polymerase. Transcripts will be subjected to limited alkaline hydrolysis to obtain a probe of approximately 150 nt. Initial experiments will establish the optimal hybridization time and temperature, washing conditions and exposure times. Riboprobes will be tritium labeled to a specific activity of $1.1 \times 10^8$ dpm/ml/kb. Sections will be autoradiographed, photographically developed, and counterstained with hematoxylin and eosin prior to microscopic observation using brightfield and darkfield optics. RNA preservation of the specimens will be assessed using a 1.8 kb probe directed against actin mRNA. In situ hybridization data will be analyzed using both bright-field morphology as well as darkfield optics to better visualize the full distribution of silver grains making up the autoradiographic signal.

Reverse Transcriptase PCR.

RNA will isolated from confluent cells (NHBE; Clonetics) harvested by trypsinization. $10^7$ cell aliquots will be disrupted in lysis buffer (1% β-mercaptoethanol and guanidine isothiocyanate) and homogenized using QIA shredder spin columns (Qiagen, Valencia, Calif.). Lysate will be treated with 70% ethanol (1:1 v:v), applied to a RNeasy mini spin column (Qiagen), washed, eluted by centrifugation (10,000 g; 1 min) in 30 µL deioinized RNase-free water and quantified by spectrophotometry. Aliquots of RNA will be mixed with specific upstream and downstream or nested downstream primers and deoxynucleotides in RT-PCR buffer (ProStar HF single-tube RT-PCR system, Stratagene, La Jolla Calif.). For rhinovirus (an RNA virus), isolation will be carried out as described above on specimens frozen immediately after collection (−70° C.) with addition of 40 U RNase inhibitor (RNasin; Promega, Madison, Wis.) according to the method os Blomqvist, et al. Moloney murine leukemia virus reverse transcriptase will be added to each reaction, with the exception of control reactions used to evaluate for DNA contamination of the isolated RNA. In a control lane, standard primers for the housekeeping gene such as glutaraldehyde phosphate dehydrogenase (GAPDH) will be added. 0.5 µl of TaqPlus Precision DNA polymerase will then be added and reaction mixtures placed in a thermal cycler and subjected to the following program: 37° for 15 minutes to synthesize cDNA, 95° for 2 minutes to deactivate the reverse transcriptase, and then 30 cycles of 95° (30 sec), 58° (30 sec) and 68° (2 min), with a final 72° 10 minute extension step. The PCR products will be analyzed by ethidium bromide stained 1% agarose gel electrophoresis in comparison to a 100 bp DNA ladder (GIBCO BRL, Grand Island, N.Y.).

Airway Acidification is Associated With $NO_2^-$ and $ONOO^-$ Protonation in vivo.

As a first step, experiments will be designed to demonstrate that pH is a critical determinant of $HNO_2$ formation/airway NO evolution in subjects with acute asthma exacerbation in vivo. It has been reported that endogenously acidified breath condensate protonates $NO_2^-$ ex vivo, decreases breath condensate $NO_2^-$ concentrations, is associated with increased expired NO concentrations and toxifies endogenous $NO_x$ as predicted by reaction (1). This experiment extends those observations to demonstrate that buffering endogenous airway acid inhibits reactions in vivo. Further, this buffering experiment may also have direct therapeutic implications for patients experiencing acute asthma exacerbations.

Phosphate buffer (10 mM) prepared in 10 mM normal saline (PBS) by the research pharmacist will be filtered (0.22 µm) and cultured to ensure sterility. Ten patients with acute asthma exacerbations (characterized by a moderate increase in cough and wheeze, an $FEV_1$ of 40–70% predicted and a breath condensate pH<7.0) will be compared with 10 subjects with asthma who are not having an acute exacerbation (asymptomatic; $FEV_1$>70% predicted) and whose breath condensate pH is >7.0, as well as with 10 healthy, control subjects (breath condensate >7.0). Subjects with acute asthma exacerbations will be excluded if they are frankly dyspneic, have a respiratory rate >28 breaths/min, or have a room air oxygen saturation value, <96%. Each subject will be given 0.05 mL/kg PBS by Pari-LC-plus nebulizer. Expired NO will be measured according to ATS standards (NIOX; Aerocrine AB; Sweden), before treatment and at 5, 10, 20, 30 and 40 min after treatment.

Models for repeated measures (multiple time points) will be used to test the hypothesis that expired NO over time differs among asthmatic subjects having an acute asthma exacerbation, asthmatic subjects not having an acute exacerbation and healthy (control) subjects. Specifically, random coefficient models, which allow for subject heterogeneity in NO profiles over time, will be used to compare the groups. The time by group interaction is of primary interest as this term describes how the time course of expired NO differs among the groups. Standard statistical software (SAS PROC MIXED) will be used to carry out the analyses, including adjustments (Kenward-Roger small sample corrections) to account for the relatively small sample sizes in these experiments.

Effect of Experimental HRV Infection on Breath Condensate $NO_x$.

A fall in pH associated with HRV 16 infection will result in NO protonation and loss of relatively water-insoluble $NO_2^-$ from solution (Reaction 1) as well as nitration of cellular proteins through $ONOO^-$ protonation. We will demonstrate that these cytotoxic reactions are more likely to occur in asthmatic subjects than controls because of the greater concentrations of $NO_x$ salts in the asthmatic airway.

30 Adult subjects with (n=15) and without (n=15) asthma associated with IgE>200 u/mL (who are seronegative and culture/PCR negative for HRV 16) will be admitted to the general clinical research center (GCRC) and inoculated with 2.5 mL/nostril of 500 $TCID_{50}$ units/mL of HRV 16. Subjects will be assessed daily for four days for twin infection by nasal washing for HRV 16 culture. Breath condensates will be collected through a 0.3 μm filter (as well as using a simple saliva trap) at baseline, then daily for four days, then weekly until three weeks after the initial inoculation. pH and $NO_2^-$ levels will be measured on the filtered condensates, as will amylase on the unfiltered specimens. Nitrated protein residues will be quantitated on the unfiltered specimens according to the method of Hanazawa and reported per mg protein. Random coefficient models will be used to compare daily profiles of nitrite ($NO_2^-$) levels following HRV16 inoculation between healthy controls and asthmatic subjects experiencing a fall in breath condensate pH.

Intrathoracic Airway ECP and pH in Asthmatic Subjects Infected With HRV 16 Who Have Low Breath Condensate pH.

This experiment will provide 1) additional direct confirmation of the relevance of condensed expired air measurements to intrathoracic airway pH; and 2) direct evidence that a fall in intrathoracic airway pH associated with HRV 16 infection causes release of eosinophilic mediators uniquely in subjects with asthma. Intrathoracic airway pH will be lower, and bronchoalveolar lavage (BAL) ECP levels will be higher, in those high IgE-asthmatic subjects who have a fall in breath condensate pH 72 hours following HRV 16 inoculation than 1) they were before HRV 16 challenge; and 2) in control subjects before and after HRV 16 challenge.

Subjects will be admitted to the GCRC and challenged with HRV 16 according to the protocol described above. A subset of ten subjects with mild, high IgE (>200 u/mL) associated asthma and ten healthy controls will be separately recruited from this group to undergo flexible bronchoscopy before and 72 hours after HRV 16 inoculation. Eight subjects in each group will be anticipated to complete this study. pH will be measured using neutral, sterile filter paper introduced with forceps through the bronchoscope into trachea, the right and left mainstem bronchi, allowed to become saturated with airway lining fluid, removed and assayed on a micro pH system. Bronchoalveolar lavage will be performed in accordance with established guidelines and using $NO_x$-free saline to lavage a subsegment of the right middle lobe (first bronchoscopy) and lingula (second). The fluid will undergo centrifugation (8,000 g; 5 min) and the supernatant will be frozen for ECP measurement.

A one-sample t-test will be used to compare ECP levels pre- and post-HRV 16 inoculation among subjects experiencing a fall in breath condensate pH. A two-sample t-test will be used to compare the pre- and post-HRV16 changes to those observed in healthy controls. Based on our preliminary data regarding breath condensate pH and upper airway ECP levels, eight high IgE-asthmatic subjects and 8 control subjects will give us >90% power to detect differences in pH and ECP, when the true difference is equal to the difference observed in the preliminary data. To correlate breath condensate to airway pH, mixed models will be used to estimate the association and to account for the correlations induced by having multiple pH samples per subject.

Relationship of Bronchoalveolar Lavage ECP Levels to Bronchoalveolar Lavage $NO_2^-$ and Nitrotyrosine Levels.

Levels of inert $NO_x$ are elevated in the asthmatic airway at baseline. With acidification, these species become cytotoxic, causing eosinophil necrosis in vitro. This experiment is designed directly to demonstrate the relevance of these reactions to the mechanism by which HRV infection and airway acidification leads to release of inflammatory mediators in vivo. In BAL fluid of asthmatic patients experiencing an HRV 16 infection, ECP levels are anticipated to be inversely related to $[NO_2^-]$ and directly related to $[ONOO^-]$. Additionally, $[NO_2^-]$ and $[ONOO^-]$ in breath condensates are anticipated to vary directly with $[NO_2^-]$ and $[ONOO^-]$, respectively, in BAL.

Lower airway pH will be measured, and BAL performed, following HRV 16 infection as described above. Nitrite and 3-nitrotyrosine (3NT)/mg protein (reflecting $ONOO^-$ protonation) will be measured. Standard correlation and regression analyses will be used to measure the association between changes in ECP (dependent variable) levels and $NO_2^-$ and $ONOO^-$ (independent variables) in asthmatic subjects experiencing a fall in breath condensate pH.

EXAMPLE 4

Airway Acidification is Associated With Airway Narrowing in Subjects with Asthma, but not in Controls.

Only patients with asthma will experience worsening expiratory airflow limitation associated with a fall in airway pH. Because patients with asthma have a uniquely pH-sensitive airway environment, they will experience increased airways inflammation and swelling following HRV-induced acidification. This will be manifest physiologically as increased air trapping caused by narrowing of the caliber of small airways in patients with asthma, but not in controls. Measurement of RV and $R_{aw}$ are very sensitive tests for expiratory flow limitation, and may identify asthmatic changes even in the absence of a change in $FEV_1$/FVC. Therefore, increase in expiratory flow limitation will be greater in patients with high IgE asthma who have a fall in breath condensate pH than 1) in patients with asthma who do not have a change in breath condensate pH; or 2) in control subjects following HRV 16 infection.

Patients will be enrolled and studied as described in Example 1. $FEV_1$/forced vital capacity (FVC) ratio, residual volume (RV) and airway resistance ($R_{aw}$) will be measured by spirometry and plethysmography according to ATS guidelines. Physiological measurements will be made before HRV 16 infection and again at 72 hours following infection. For patients undergoing BAL, these measurements will be made before the bronchoscopy.

One-way analysis of variance will be used to test for changes in RV, $FEV_1$/FVC and $R_{aw}$ among asthmatic subjects experiencing a fall in pH, asthmatic subjects not experiencing a fall in pH and control subjects. The specific comparisons of primary interest are comparing asthmatic subjects with a fall in pH to subjects in each of the other two groups. Separate analyses will be done for each endpoint, with a Bonferroni correction to the critical values to account for the multiple tests.

The Relationship Between Change in Breath Condensate pH and Degree of Obstruction.

We predict that breath condensate pH will be an important determinant of airflow obstruction following HRV infection in patients with allergic asthma. As such, we predict that degree of change in acidity will predict the degree of obstruction.

Residual volume to total lung capacity (TLC) ratio, $FEV_1$/FVC ratio, fraction of unventilated lung area in a single coronal mid-plane lung section studied by single-breath hyperpolarized Helium MRI and breath condensate pH will be studied before, and 72 hours following, infection of patients with allergic asthma with HRV 16. Standard correlation and regression analyses will be used to estimate the association between pH levels and degree of obstruction in subjects with allergic asthma. The addition of nonlinear terms to the model will be used to test the assumption of a linear relationship between obstruction and pH levels.

Relationship Between Lower Airway Acidification-related Cytotoxicity and Air Trapping.

We anticipate that low airway pH will be associated with increased cytotoxicity in the asthmatic airway, that neutralization of airway acid will inhibit this cytotoxicity, and that low airway pH following HRV 16 infection will be associated with the development of air trapping. Thus, we will complete the analysis of the pathway by demonstrating directly that increased acidosis-related cytotoxicity is associated with air trapping in allergic asthma.

Plethysmography and BAL will be performed before and after HRV 16 on eight subjects with high IgE asthma. Plethysmography will be performed before bronchoscopy. Change in RV/TLC will be studied as a function of change in ECP levels. Standard correlation and regression analyses will be carried out to investigate the association between changes in RT/TLC and ECP levels.

EXAMPLE 5

Determination That Airway Acid is Buffered by $NH_3$, a Product of Epithelial Glutaminase.

Acute Asthma Exacerbations and Airway Acidification are Associated with a Fall in $NH_4^+$ Concentrations in Both Exhaled Breath Condensate and Bronchoalveolar Lavage Samples.

This study will confirm our preliminary observations that low breath pH is accompanied by low breath $NH_4^+$ levels in subjects with acute asthma, suggesting that impaired $NH_4^+$ production may lead to acidification in the airway, as it does in the renal tubular epithelium.

Twenty patients, four through 18 years old, presenting to the emergency department between September and December who have active, β2 agonist-reversible wheezing and meet NHLBI Expert Board guidelines for a diagnosis of asthma will be enrolled and asked to perform a breath condensate collection as previously described by our group. These subjects will be compared with a control group of wheeze-free children in the same age range who have no history of asthma. Patients will be excluded from both groups if they have a history of hepatic, renal, metabolic, chronic inflammatory or acute infectious disease. pH values will be measured as previously described, and $NH_4^+$ levels will be measured spectrophotometrically. Values of $NH_4^+$ from subjects with asthma and low pH will be compared with those from control subjects.

Standard regression models will be used to estimate the association between $NH_4^+$ levels and pH levels in asthmatic and control patients. The first regression model will have $NH_4^+$ levels as the dependent variable and terms for group, pH level and a group by pH level interaction.

Airway Epithelial Cells Express Glutaminase That is Upregulated by Corticosteroids.

Human Airway Epithelial Cells Transcribe the Glutaminase Gene.

Transcription of genes for glutaminase by airway epithelial cells has not previously been demonstrated or studied. However, our preliminary data demonstrate that glutaminase is transcribed and active in proximal human airway epithelial cells, and that its activity is relevant to the asthmatic response to viral infections. This experiment will demonstrate transcription of the gene in human primary cell culture lines from the distal airway.

RNA will be extracted from A549 and SAEC cells grown to confluence in six-well plates as previously described. Primers constructed from the sequence for GAC and KGA isoforms of human glutaminase, as well as glyceraldehyde phosphate dehydrogenase (GAPDH; housekeeping) will be used to amplify a cDNA probe by reverse transcriptase PCR (RT-PCR). These RT-PCR products will be labeled with $^{32}P$ and used to probe mRNA from normal human bronchial epithelial (NHBE) cells and small airway epithelial cells (SAEC) in Northern blot analysis. Glutaminase mRNA will be identified by Northern blot and compared with that for GADPH by densitometry. A two-sample t-test will be used to compare mean glutaminase mRNA by densitometry to GADPH.

Detection of Glutaminase RNA by in situ Hybridization.

If glutaminase is an important determinant of HRV-initiated airway pH changes and asthma exacerbations, it is likely to be downregulated transcriptionally by cytokines such as IFN γ (as is evident in other systems and in vitro in the airway). This experiment will provide direct in vivo evidence for this concept.

Patients undergoing bronchoscopy before and after HRV 16 infection will have endobronchial epithelial biopsies obtained from the trachea and mainstem bronchi (n=3 biopsies from each at baseline and 72 hours after infection). Each biopsy will be studied for epithelial glutaminase mRNA (pro-mRNA can be used because of the post-transcriptional differentiation of glutmaminase isoforms) by in situ hybridization. Specimens obtained from subjects whose pH has fallen to <7.0 will be compared to those from patients before HRV infection and to those whose pH has not fallen to <7.0. Repeated measures models for binary data will be carried out, with one "between" factor (fall in breath pH group) and one "within" factor (biopsy location).

Effect of Hydrocortisone on Glutaminase Transcription

Glutaminase has a steroid-responsive promoter, and its expression is increased by corticosteroids in a variety of systems. This biology fits well with the observation that corticosteroids normalize airway pH in vivo and improve asthma symptoms, as well as immunohistochemical evidence for upregulation of human lung glutamine worse by systemic corticosteroids. It is anticipated that glutaminase mRNA expression and activity will be increased in airway epithelial cells in culture following treatment with hydrocortisone.

mRNA will be extracted from airway epithelial cells after each cell type is treated with hydrocortisone in a time (4, 6, 8 and 12 and 24 hours) and dose (1, 10 and 100 μM)-dependent fashion (four control wells and four hydrocortisone wells per experiment) before harvest. Glutaminase mRNA will be identified by northern blot, and compared with that for GAPDH by densitometry. Activity will be compared at each point by $NH_4^+$ assay in 2 mM glutaminase. Two factor analysis of variance will be used to investigate the dependence of glutamine mRNA on time and dose of hydrocortisone. Logistic regression models will be used to compare the probability of expression as a function of time and dose of hydrocortisone.

Effect of Airway Acid and of Interferon γ on Airway Epithelial Glutaminase Biochemical Activity.

In the renal tubular epithelium, glutaminase is upregulated post-transcriptionally by exposure to acidity in the glomerular filtrate. We propose that airway epithelial glutaminase is similarly upregulated by exposure to lumenal acid. Further, this effect of low pH on epithelial glutaminase activity should be overcome by IFN γ in vivo, consistent with observations that subjects developing acute viral infection have low breath condensate $NH_4^+$ levels in the context of low pH. Therefore it is anticipated that 1. Exposure to a pH<7.4 (an airway "threshold" for acidification) will increase glutaminase activity of human airway epithelial cells in culture; and that 2. Interferon γ will overcome this acidification effect and inhibit airway epithelial cell acidification at low and high pH.

Airway cells will be grown to confluence in six-well plates. One group of cells will be exposed to pH 6.6 and another to pH 7.5, with pH-retitrated (HCl) every 12 hours, for 72 hours. Cumulative $NH_4^+$ production in the medium will be measured. Cell culture medium alone at each pH level will serve as controls. The experiment will be repeated with 100 u/mL IFN γ in the culture medium—for the optimal time determined to see pH-induced glutaminase upregulation (above)—at low and high pH. A two-sample t-test will be used to compare the areas under the curve between the group of cells exposed to pH 6.6 and the group exposed to pH 7.5.

EXAMPLE 6

Determining That Rhinovirus Infection Decreases Airway Epithelial Glutaminase Activity.

Glutaminase Activity and Expression During HRV 16-Associated Lower Airway Acidification in vivo.

This experiment is designed to demonstrate directly the role of glutaminase (and its level of regulation) in acidifying the airway in response to an HRV infection in vivo. We predict that HRV 16 infection will decrease airway epithelial glutaminase expression and activity in vivo (even if it does not have a direct effect on epithelial cells in vitro) because of T-cell and neuronally-mediated mechanisms in the intact organism. It is anticipated that Bronchoalveolar $NH_4^+$ levels and airway biopsy expression of glutaminase will be decreased in patients with HRV 16 infection who have a fall in breath condensate pH.

Subjects will undergo breath condensate measurement, bronchoalveolar lavage and endobronchial biopsy before and after HRV 16 infection as described in SA. Change in bronchoalveolar lavage $NH_4^+$ concentration and presence or absence of glutaminase expression will be characterized as previously described, and compared before and after HRV 16 infections in patients who do and do not experience a fall in condensate pH. The two-sample t-test will be used to compare changes in $NH_4^+$ and the two-sample binomial test will be used to compare glutamine expression between groups of subjects who experience a fall in breath condensate pH and those who do not experience a fall in breath condensate pH.

Interferon γ Inhibits Intrathoracic Airway Epithelial Glutaminase Expression and Activity in vitro and in vivo.

Effect of IFN γ on Glutaminase Activity and Expression in vitro

This experiment is designed to identify the optimal conditions at which IFN γ, the primary candidate cytokine known to inhibit glutaminase in other systems, inhibits glutaminase in airway epithelial cells. The design of this experiment will be similar to that of Example 2, except that 1) all experiments will be done at pH 7.14, and 2) a dose response (1, 10, 100 and 500 u/mL) and time course (6, 12, 24, 48 hr) for the effect of IFN γ on all cells lines will be evaluated. We anticipate that IFN γ will inhibit glutaminase in a dose-and time dependent fashion, and that this inhibition will be transcriptional.

In addition, condensed expired air pH and $NH_4^+$ concentration are both expected to decrease following IFN γ therapy for idiopathic pulmonary fibrosis (IPF). Bronchoalveolar lavage fluid will be obtained before and after HRV 16 infection and analyzed for IFN γ concentration. Levels in subjects whose condensed expired air pH falls will be compared with those from subjects whose pH does not change, and with values before infection. We propose that Th1 (and/or CD 8) lymphocyte activation (whether in the airway or systemically) in response to HRV infection will increase BAL IFN γ levels. Also, a greater fall in subjects who acidify will be consistent with the preceding experiments demonstrating a role for IFN γ in inhibiting glutaminase and regulating airway pH.

Effect of S-nitrosoglutathione (GSNO) on Glutaminase Activity in Airway Epithelial Cells.

S-Nitrosylation reactions are increasingly appreciated to cause functional post-translational modifications of proteins with critical cysteine residues. This is particularly true of mitochondrial enzymes such as glutaminase. S-Nitrosoglutathione is an endogenous S-nitrosylating agent that may be produced by nonadrenergic (noncholinergic) (NANC) neuronal stimulation and by inflammatory cells. As such, inhibition of glutaminase by S-nitrosylation reactions could be a mechanism by which an autonomic and/or inflammatory HRV-infected nasal mucosa to the lower airway mucosa to inhibit glutaminase and lower pH.

A549, NHBE and SAEC cells will be grown to confluence in 6 well plates in the presence of 2 mM glutamine and exposed to 0.5, 1, 10 and 100 μM GSNO for 4, 8 and 12 hours. Cumulative $NH_4^+$ production will be determined colorimetrically. If there is inhibition of glutaminase activity, the effect of 100 μM dithiothreitol in reversing, and of 8 bromo cyclic GMP in reproducing, this effect will be studied. Within each cell line, two-factor analysis of variance methods will be used to investigate the effects of GSNO dose and time on activity. Similar analyses will be conducted to investigate the roles of DTT and cGMP on activity. We predict that lower airway epithelial glutaminase will be inhibited by GSNO in a time- and dose-dependent manner, that this inhibition will be reversed by DTT and that it will not be reproduced by 8-Br cGMP.

Role of γGT in the Inhibition of Glutaminase by GSNO.

It has been reproted that γGT is critical for the bioactivation of GSNO in several models, including regulation of nuclear transcription factors and control of breathing. Additionally, GSNO catabolism, mediated by γGT, may be accelerated in allergic asthma. We therefore anticipate that γGT may be active in the airway epithelium, catabolizing GSNO and converting it to cell-permeable, bioactive CGSNO, which then inhibits glutaminase, allowing acidification of the airway. Defining this pathway will have important implications for developing new therapeutic agents for virally-induced asthma exacerbations. Accordingly, it is anticipated that Acivicin will prevent the inhibition of airway epithelial glutaminase activity by GSNO, and this effect will be overcome by CGSNO.

Airway epithelial cells will be grown as described and treated with 100 μM acivicin, an inhibitor of γGT. They will then be treated with GSNO and glutaminase activity will be measured. If acivicin blocks the effect of GSNO, we will examine the effect of acivicin in blocking the inhibition of glutaminase by 100 μM CGSNO. One-way ANOVA will be used to compare the groups (GSNO, GSNO with acivicin) with respect to glutaminase activity EXAMPLE 7
Practical Applications of the Present Invention 1. A 16 year old girl with moderate asthma develops an upper respiratory infection associated with wheezing and dyspnea. She receives treatment with albuterol. 0.083 mg diluted in normal saline (pH 3.5) but her symptoms do not improve. She then receives another treatment with the same dose of albuterol diluted in 10 mM phosphate buffered saline, pH 8, and her symptoms resolve.

2. A 45 year old man with severe asthma who becomes dyspneic whenever he develops an upper respiratory infection uses glutamine, 1 gm by nebulizer (pH 8) twice a day at the onset of upper respiratory symptoms. He does not develop an asthma exacerbation.

3. The same patient described in number 2 above develops an upper respiratory infection the following winter. He takes glutamine, 1 gm by mouth three times a day and does not develop any asthma symptoms.

4. A 36 year old woman with severe asthma is unable to walk more than 200 yards because of shortness of breath and stays up most nights coughing. She is treated with levalbuterol and budesonide, 0.5 mg by nebulizer four times/day without relief of her symptoms. She begins receiving 1 mM glycine in 10 mM CAPS (pH 7.6) by nebulizer immediately before her levalbuterol and budesonide treatments, and she becomes asymptomatic, with unlimited exercise tolerance and no cough at night.

5. A 50 year old woman with chronic yeast infection in her mouth has worsening asthma. She is treated with a 7 day course of fluconazole 200 mg/day and her asthma symptoms improve because of elimination of acetic acid-producing organisms.

6. The same woman described in number 5 above becomes recolonized with a fermenting organism. Her asthma symptoms recur. She is treated with 10 mg disulfiram by nebulizer 3 times/day to inhibit airway aldehyde dehydrogenase activity. Her symptoms resolve.

7. A 5 year old boy with an upper respiratory infection-associated asthma exacerbation is treated with 10 μM CuCl in 10 mM phosphate buffered saline, pH 8, three times/day to break down glutaminase-inhibiting S-nitrosothiols. His asthma symptoms resolve.

8. A 40 year old woman with HIV is exposed to a friend with active pulmonary tuberculosis. She receives 1 mM diazo-5-oxo-L-norleucine (to inhibit glutaminase) in HCl (pH 2) by nebulizer three times daily for a month and does not develop tuberculosis.

9. A 2 year old girl contracts active pulmonary tuberculosis caused by an organism resistant to conventional antimicrobial agents. She is begun on a low-glutamine diet and receives acetic acid (pH 3) by nebulizer four times daily for 9 months. Her symptoms resolve, and mycobacteria can no longer be identified in her respiratory secretions.

What is claimed is:

1. A method for enhancing the therapeutic efficacy of one or more agents, selected from the group consisting of albuterol, levalbuterol HCl and ipratroprium bromide, used in the treatment of one or more airway diseases selected from the group consisting of asthma, asthma exacerbations, smooth muscle constriction, airway inflammation, overproduction of mucus, human rhinovirus infection, common cold, allergic rhinitis, tuberculosis, cough, wheeze and airtrapping, said method comprising combining at least one non-toxic, alkaline composition, selected from the group consisting of acetate salts, ammonium salts phosphate salts, bicarbonate salts, glycine and glutamine, in a nebulized form with said conventional agent immediately prior to bringing the resulting combination into contact with a patient's airways such that the resulting combination has a pH of at least 7.4 and no more than 10.0.

2. The method of claim 1 wherein the airway disease being treated is asthma.

3. The method of claim 1 wherein said alkaline composition further includes a basic buffer having an alkaline pKa in a nebulized form.

4. The method of claim 3 wherein said buffer is selected from one or more of the group consisting of acetate salts, ammonium salts, phosphate salts, bicarbonate salts, glutamine, glycine (aminoacetic acid), $pK_a2 = 9.78$), bicine (N,N-Bis(2-hydroxyethyl)glycine ($pK_a=8.46$), tricene (N-[tris(hydroxymethyl)methyl] glycine ($pK_a=8.26$), CAPS (3-(Cyclohexamino)-1-propanesulphonic acid (10.51). CAPSO (3-(Cyclohexamino)-2-hydroxypropanesulphonic acid ($pK_a32$ 9.71), and 2-(Cyclohexamino)-ethenesulphonic acid ($pK_a=9.41$).

5. The method of claim 4 wherein said buffer is a natural or synthetic, non-toxic base.

6. A method for enhancing the therapeutic efficacy of one or more corticosteroids, selected from the group consisting of hydrocortisone, dexamethasone and budesonide, used in the treatment of one or more airway diseases selected from the group consisting of asthma, asthma exacerbations, smooth muscle constriction, airway inflammation, overproduction of mucus, human rhinovirus infection, common cold, allergic rhinitis, tuberculosis, cough, wheeze and airtrapping, said method comprising combining at least one non-toxic, alkaline composition, selected from the group consisting of acetate salts, ammonium salts, phosphate salts, bicarbonate salts, glycine and glutamine, in a nebulized form with said corticosteroid immediately prior to bringing the resulting composition into contact with a patient's airways or concurrently therewith, such that the resulting composition has a pH of at least 7.4 and no more than 10.0.

7. The method of claim 6 wherein the airway disease being treated is asthma.

8. The method of claim 6 wherein said alkaline composition further includes a basic buffer having an alkaline pKa in a nebulized form.

9. The method of claim 8 wherein said buffer is selected from one or more of the group consisting of acetate salts, ammonium salts, phosphate salts, bicarbonate salts, glutamine, glycine (aminoacetic acid), $pK_a2 = 9.78$), bicine (N,N-Bis(2-hydroxyethyl)glycine ($pK_a=8.46$), tricene (N-[tris(hydroxymethyl)methyl] glycine ($pK_a=8.26$), CAPS (3-(Cyclohexamino)-1-propanesulphonic acid (10.51), CAPSO (3-(Cyclohexamino)-2-hydroxypropanesulphonic acid ($pK_a9.71$), and 2-(Cyclohexamino)-ethenesulphonic acid ($pK_a=9.41$).

10. The method of claim 9 wherein said buffer is a natural or synthetic, non-toxic base.

* * * * *

UNITED STATES PATENT AND TRADEMARK OFFICE
CERTIFICATE OF CORRECTION

PATENT NO. : 6,930,125 B2
DATED : August 16, 2005
INVENTOR(S) : John F. Hunt and Benjamin M. Gaston It is certified that error appears in the above-identified patent and that said Letters Patent is hereby corrected as shown below:

Column 22,
Line 14, delete "conventional".

Signed and Sealed this

Twenty-seventh Day of September, 2005

JON W. DUDAS
*Director of the United States Patent and Trademark Office*